United States Patent
Kouznetsov et al.

(10) Patent No.: US 6,526,801 B2
(45) Date of Patent: Mar. 4, 2003

(54) METHOD OF COMPENSATING FOR DRIFT IN GAS SENSING EQUIPMENT

(75) Inventors: Andrian Kouznetsov, Santa Barbara, CA (US); Audrey Nelson, Goleta, CA (US); Brian C. Maddux, Goleta, CA (US); Don Q. Higgins, Santa Barbara, CA (US); Jean A. Nisbet, Goleta, CA (US)

(73) Assignee: Edwards Systems Technology, Inc., Cheshire, CT (US)

( * ) Notice: Subject to any disclaimer, the term of this patent is extended or adjusted under 35 U.S.C. 154(b) by 0 days.

(21) Appl. No.: 09/751,668

(22) Filed: Dec. 29, 2000

(65) Prior Publication Data

US 2002/0121126 A1 Sep. 5, 2002

(51) Int. Cl.[7] .............................. G01N 21/00
(52) U.S. Cl. ....................... 73/1.03; 702/104
(58) Field of Search ............... 73/1.03, 23.21, 73/23.28; 702/104, 86, 87, 89

(56) References Cited

U.S. PATENT DOCUMENTS

| 4,686,638 | A | * | 8/1987 | Furuse ..................... 364/558 |
| 5,347,474 | A | | 9/1994 | Wong ..................... 364/571.02 |
| 5,550,737 | A | * | 8/1996 | Tedeschi ................. 364/424.03 |
| 5,594,667 | A | | 1/1997 | Myers .................... 364/571.01 |
| 5,612,896 | A | * | 3/1997 | Stock ......................... 364/497 |
| 5,659,125 | A | | 8/1997 | Ernst ........................... 73/1.03 |
| 5,746,122 | A | * | 5/1998 | Gietz et al. .................... 100/43 |
| 6,112,161 | A | * | 8/2000 | Dryden et al. ................ 702/85 |

* cited by examiner

Primary Examiner—Hezron Williams
Assistant Examiner—Charles D Garber
(74) Attorney, Agent, or Firm—Baker & Hostetler LLP

(57) ABSTRACT

A method for compensating for baseline or span drift in gas sensing equipment includes obtaining gas concentration data over a time period and identifying a quiescent period within that time period. The method compares a component concentration corresponding to the quiescent period with one or more additional component concentrations relating to different quiescent periods and calculates an estimated background gas concentration for a predetermined number of time periods. The estimated background concentration is then compared to a preset, or expected, background concentration, and a correction value is calculated. For baseline drift, a correction value is determined to be the difference between the estimated background concentration and the present (expected) background concentration. For span drift, a correction value is determined to be the ratio of the estimated background concentration to the preset (expect) background concentration. Measured concentrations by the gas sensor are then adjusted by the correction value.

19 Claims, 3 Drawing Sheets

METHOD OF COMPENSATING FOR DRIFT IN GAS SENSING EQUIPMENT

FIELD OF THE INVENTION

The present invention relates generally to gas sensing equipment and calibration methods associated therewith. More particularly, the present invention relates to digitally-implemented methods for identifying and preventing "drift," or unwanted and inaccurate changes in the readings, of the gas sensing equipment.

BACKGROUND OF THE INVENTION

Gas sensors are commonly used to measure the presence of one or more elements or components in a gas mixture. For example, a gas sensor may be used to measure the concentration of one or more pollutants in ambient air in an indoor or outdoor environment. Other examples may include flue gas monitoring, combustion processes control, fire alarms, gas leak detectors, and other applications where gas sensing is required. Such sensors are often connected to process control and monitoring equipment, or they may be connected to alarms that are triggered when concentrations of a measured gas exceed a predetermined limit, such as a desired limit based on worked protection guidelines or applicable regulations, or a health-based limit that is derived from research in the field.

A carbon dioxide ($CO_2$) monitor, which measures the concentration of $CO_2$ in ambient air, is one such gas sensor. Typically, $CO_2$ monitors continuously measure $CO_2$ concentrations in the subject environment and are connected to a ventilation control system to ensure appropriate ventilation rates. The nature of many environments, such as offices, stores, and industrial environments, results in a cyclical $CO_2$ level in the environment at various points in the day. For example, an office area may experience its highest $CO_2$ levels in the middle of the afternoon, when most $CO_2$ sources (i.e., the office workers) are in the office and have been present for a period of time. Such an environment may experience its lowest $CO_2$ levels in the wee hours of the morning, after most or all of the workers have departed from the previous day and before most or all the workers have arrived for the day.

Moderate natural background levels of $CO_2$ exist in most environments. Thus, even when most or all $CO_2$ sources are not present, as when all workers have departed from an office, a background level of $CO_2$ typically remains. Thereafter, the background level may be considered to be a baseline against which measurements of concentrations in ambient air may be made.

Such background levels also exist in many environments for components other than $CO_2$. For example, very low levels of carbon monoxide (close to 0.1 ppm) exist in most environments under normal conditions, and carbon monoxide alarms thus must be able to distinguish a measured concentration from almost zero levels of carbon monoxide.

One drawback of the prior art gas sensors is that such sensors typically experience a phenomenon known as "drift." Drift is a slow change of the properties of the sensor components, resulting in a gradual reduction in the accuracy of the sensor. Drift may be caused by any number of external factors, such as gradual chemical changes, a build-up of foreign matter over time and aging of the sensor components. The inaccuracy of the sensor is normally associated with changes in two sensor calibration parameters: baseline (zero readings) and span (calibration point). For many types of sensors, only one type of inaccuracy may dominate. Thus, for example, for one type of sensor an inaccuracy may be caused by the sensor zero drift, while another type of sensor may be inaccurate because of span drift. For example, it is well known that non-dispersive infrared (NDIR) gas sensors often primarily exhibit zero drift, while photo-acoustic infrared gas sensors typically have span drift as a dominating factor of inaccuracy.

A typical method for reducing or eliminating drift in a gas sensor is to either construct it to have high accuracy or to manually recalibrate the sensor on a periodic basis. Gas sensor re-calibration normally requires the use of at least one calibration gas mixture. Either option leads to increased costs, and both methods can be unreliable due to equipment failure and/or human error. Moreover, many applications require unattended sensor operation for very long periods of time, and thus frequent re-calibration is not desirable.

One method of compensating for drift of a gas sensor is disclosed in U.S. Pat. No. 5,347,474, to Wong. In particular, columns 3–6 of Wong, incorporated herein by reference, disclose a method of calibrating a carbon monoxide sensor. However, we have determined that alternate methods are desirable and preferable.

Therefore, we have determined that it is desirable to provide a method of automatically compensating for drift in gas sensors.

SUMMARY OF THE INVENTION

It is therefore a feature and advantage of the present invention to provide a method of automatically compensating for baseline and/or span drift in gas sensors.

One embodiment of the present invention is a method that includes providing a processor, such as an embedded microprocessor, with gas concentration data relating to a first period of time. The method includes identifying a quiescent period, which a subset of the first period of time. The gas concentration data that relates to the first period of time includes quiescent period data relating to the quiescent period. The method also includes determining a first component concentration, as well as providing the processor with at least one additional component concentration. Each additional component concentration corresponds to a separate and distinct time period. The first component concentration and the additional component concentrations provide an initial concentration set. The method also includes selecting, by the processor, at least one valid concentration from the initial concentration set. The selected valid concentrations yield a valid concentration set. The method also includes providing the processor with a preset background value, calculating, by the processor, an estimated background value, and calculating, by the processor, a correction value. The correction value in one embodiment may equal the difference between the preset background value and the estimated background value. Alternately, the correction value may equal the ratio of the preset background value to the estimated background value.

The method also includes the step of detecting a measured component concentration and adjusting the measured component concentration, the adjustment corresponding to the correction value, to yield an adjusted component concentration.

Optionally, the quiescent period has duration, and the duration is equal to or greater than a minimum duration, and the estimated background value relates to the quiescent period data, such as an average of some or all of such data.

As an alternative option, the quiescent period has a duration, the duration is less than a minimum duration, and the first component concentration is omitted from the valid concentration set.

As an additional option, it may occur that the first component concentration does not correspond to a predetermined value, in which case the first component concentration may be omitted from the valid concentration set. In this option, it is a further option that the predetermined value may relate to one or more of the additional component concentrations.

As additional options, the estimated background concentration may correspond to the valid concentrations in the valid concentration set, such as an average of some or all of such concentrations. Further, the method may include the additional step of triggering an event or selecting a restriction if the correction value exceeds a trigger value.

In accordance with an additional embodiment of the present invention, a system for compensating for gas sensor drift includes a processor and a memory for storing data to be processed by the processor. The processor is programmed to perform steps including accepting gas concentration data relating to a first time period. The steps also include identifying a quiescent period, where the quiescent period is a subset of the first time period. The gas concentration data includes quiescent period data relating to the quiescent period. The steps also including determining a first component level, accepting, from data stored in the memory, at least one additional component level, where each additional component level relates to an additional time period. The steps also include providing an initial component set that includes at least one of the first component level and one or more of the additional component levels. The steps also include selecting at least one valid component level from the initial component set to yield a valid component set; accepting, from the data stored in the memory, a preset background level; calculating an estimated background level; and calculating a correction value. Optionally, the correction value equals the difference between the preset background level and the estimated background level. Alternatively, the correction value equals the ratio of the preset background level to the estimated background level.

Optionally, the first component level relates to the quiescent period data. As an additional option, the estimated background level corresponds to the valid component levels in the valid component set, such as an average of some or all of such values. The processor may also be programmed to perform the step of detecting a measured component concentration and adjusting the measured component concentration, the adjustment corresponding to the correction value, to yield an adjusted component concentration. Also optionally, the processor is programmed to perform the step of triggering an event if the correction value exceeds a trigger value.

In accordance with an alternate embodiment of present invention, a method for compensating for the drift of gas sensing equipment includes gathering gas concentration data relating to a plurality of time periods and identifying a plurality of quiescent periods. Each quiescent period is a subset of the one of the time periods. The gas concentration data relating to each time period includes quiescent period data relating to the corresponding quiescent period. The quiescent period data includes data corresponding to a background concentration. The method also includes collecting the background concentrations for each quiescent period in an initial concentration set, validating the background concentrations in the initial concentration set to yield valid concentrations in a valid concentration set, identifying a first component level, calculating a second component level corresponding to the valid concentrations in the valid concentration set, calculating a correction value corresponding to a function of the first component level and the second component level, detecting a measured component concentration, and adjusting the measured component concentration corresponding the correction value to yield an adjusted component concentration. Optionally, the function in the calculating step is a difference or a ratio.

There has thus been outlined, rather broadly, the more important features of the invention in order that the detailed description thereof that follows may be better understood, and in order that the present contribution to the art may be better appreciated. There are, of course, additional features of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION OF PREFERRED EMBODIMENTS OF THE INVENTION

The present invention is a novel automated drift compensation method and system as herein disclosed. The method and system may be used with any sensor that experiences a dominating drift mechanism, including baseline (zero) drift and/or span (gain) drift. The preferred embodiment described below is useful with, for example, indoor $CO_2$ measurements and heating, ventilation, and air conditioning ("HVAC") system control using an NDIR gas sensor. However, the described application is only exemplary, and the method and system may be used with any type of gas sensing equipment.

Figure 1:
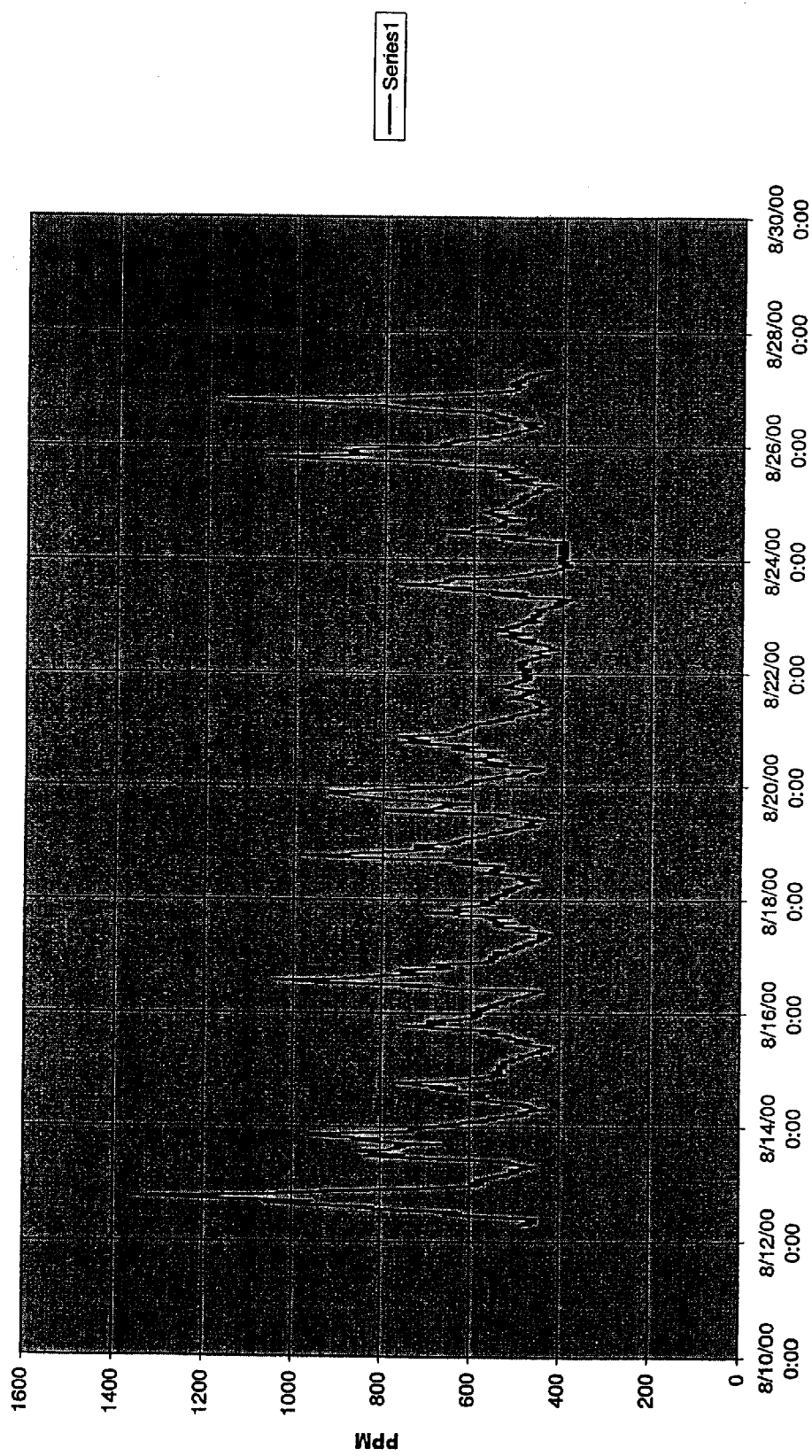
FIG. 1 is a chart illustrating exemplary typical variations in a component concentration in indoor ambient air over a time period.

FIG. 1 shows how the measured concentration of a component in ambient air, in this illustration $CO_2$, may vary during a typical series of 24-hour cycles in a building. The data illustrated in FIG. 1 is actual data gathered in a movie theater. In the late afternoon and early evening, as customers arrive for scheduled evening movies, the $CO_2$ level increases. Thereafter, as the movies end and people leave the building, the CO2 level decreases. After the theater closes, the CO2 concentration stabilizes at a relatively low level. In a preferred embodiment herein, this low-level concentration is referred to as a quiescent value, and the period during which this low level occurs is referred to as a quiescent period. However, the present invention is not intended to be limited to minimum values, and in an alternate embodiment of the present invention, the quiescent value may be, for example, a maximum value or a specific predetermined value, and the quiescent period may be the period during which the maximum value or specific predetermined value occurs.

Similar effects may be observed in other types of buildings. For example, in an office building, early in the morning, as the workers begin to arrive, the CO2 level increases and reaches a peak at some time during the day. Thereafter, as the workers leave the office building, the CO2 level decreases. After working hours, the CO2 concentration stabilizes at a relatively low level.

During the quiescent period described herein in a preferred embodiment, the concentration of CO2 typically reaches the ambient background level which generally ranges between 350 and 500 parts per million, and which typically is about 380 parts per million. On some occasions, however, the CO2 concentration may never reach the background level in a quiescent period. This may occur because, for example, the building never was empty within a 24-hour cycle. In addition, the time periods and cycles illustrated in FIG. 1 are only intended to serve as illustrative examples, and any time period or cycle appropriate for the environment may be used. For example, some buildings operate on a 24-hour a day, five day per week cycle, with periods of inactivity over a weekend. In such buildings, the cycle may be a seven-day cycle, and the quiescent period may occur over the two-day weekend. In addition, in some other cases the quiescent period could be specifically arranged to provide a predefined gas concentration to the sensor.

With time, as monitor components age, the baseline or span of a sensor may experience drift, resulting in measurements that do not accurately reflect actual conditions. For example, NDIR CO2 monitors typically experience baseline drift, the monitor may yield readings that are increasingly higher (or lower) over a period of time. Normally drift occurs very slowly, so the sensor reading error slowly increases over several ambient air concentration cycles. It is the purpose of the present invention to compensate the monitor or sensor for this observed drift.

Figure 2:
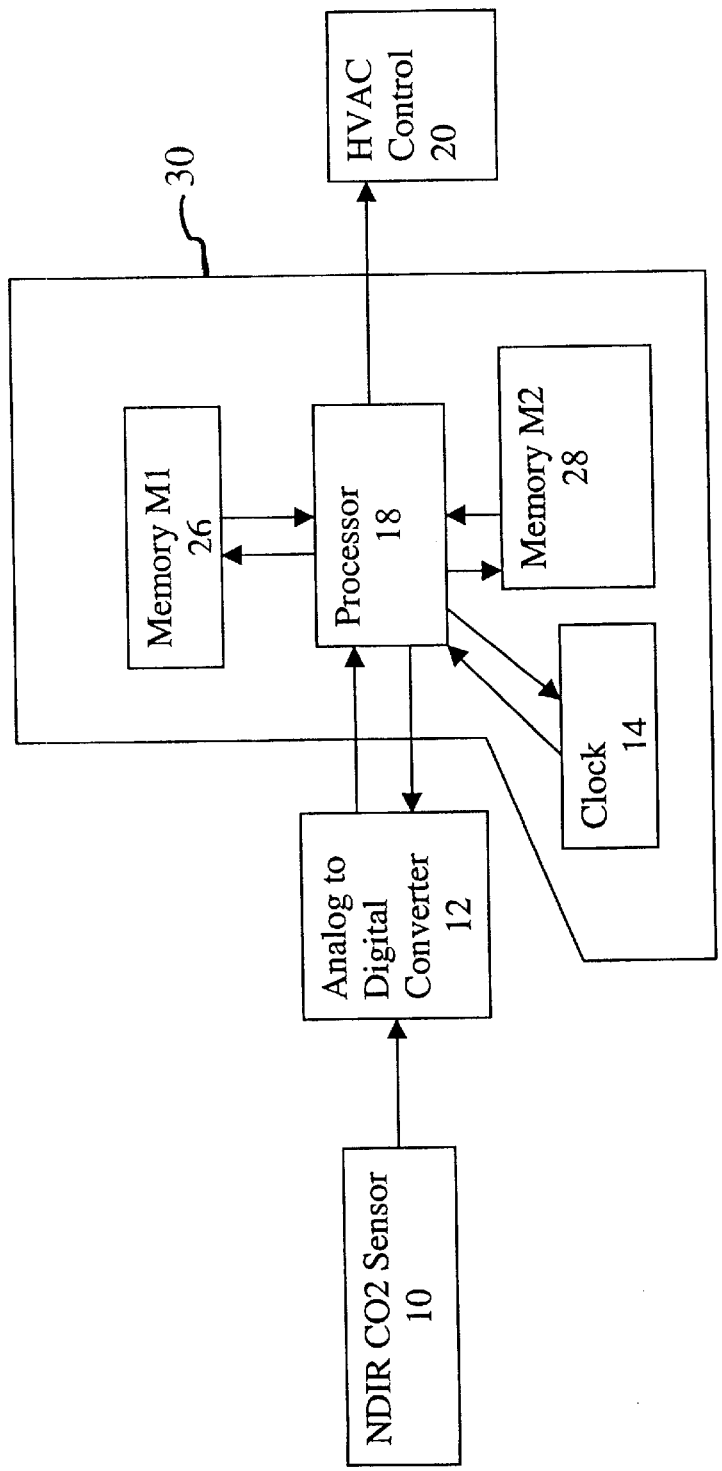
FIG. 2 is block diagram showing a preferred embodiment of a system implementing the present inventive method.

FIG. 2 illustrates a preferred embodiment of an apparatus that may be used to implement the present inventive method. Referring to FIG. 2, a sensor 10 produces an output signal x(t) that is digitized periodically by an analog-to-digital converter 12 that is enabled by a clock 14. In a preferred embodiment, the clock 14 may be part of a processing unit, such as an embedded microcomputing device 30. In a preferred embodiment, the signal digitizing is performed every second. However, any time period may be used.

The successive digitized data are fed to the processor 18. Optionally, the analog-to-digital converter 12 is not used in an embodiment where the output of the sensor is in a digital format. It is also possible that the drift compensation algorithm logic is implemented using hardware and software that is embedded in the sensor. In this case, as well as in cases where an external processor, there is no need that a processor be dedicated to drift compensation only. Rather, any processor may be used, including a processor that also serves other functions. Yet another option is to implement the method using a processor embedded in equipment that includes the sensor, such as, for example, HVAC equipment.

The processor 18 operates on the incoming X(j) data to compensate for drift of the sensor 10, producing the corresponding drift-compensated Xc(j). The drift compensated variable Xc(j) then may be applied to an external device, such as, for example, an HVAC system control 20. The HVAC system control in this example may control the operation of ventilation system by increasing or decreasing the ventilation rate depending on CO2 concentration readings Xc(j). Thus, the CO2 sensor and HVAC control are providing optimal ventilation rates for the subject office environment. The memories 26 and 28 are associated with or could be a part of the microcomputing device 30. The number of memories illustrated in FIG. 2 is optional, as a single memory, or any number of memories, may be used.

Figure 3:
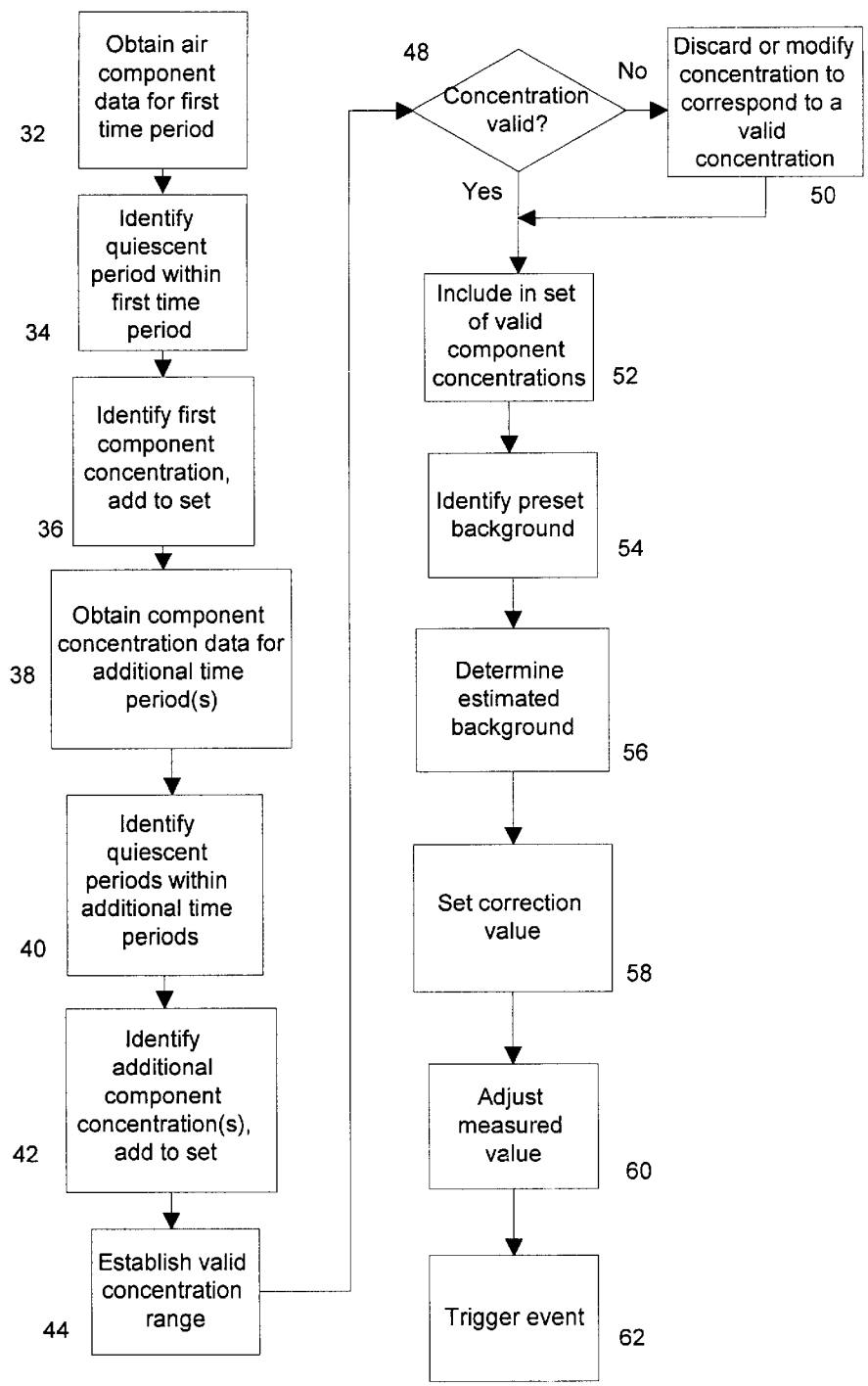
FIG. 3 is a flowchart illustrating the steps by which a calibration may be performed in a preferred embodiment of the present inventive method.

Preferred embodiments of the method by which the processor 18 compensates for drift of the sensor are shown in the flow diagram of FIG. 3 in which it is assumed, for illustrative purposes, that the variable x(t) is sampled every one second. However, any period of time may be used.

Referring to FIG. 3, in a preferred embodiment of the present invention, the system measures gas concentration data (box 32) during a time cycle and identifies the quiescent period (box 34) with minimal CO2 concentration readings within the cycle. The system cycle depends on the periodic nature of the process and the environment that is being monitored. The cycle may be, for example, a day, a portion of a day, an hour, or any predetermined time period. In the preferred embodiment described herein, the system cycle is twenty-four hours. In the preferred embodiment the quiescent period is the period of time within the cycle when the CO2 concentration remains stable within a predefined concentration range, for example +/−20 ppm CO2. In a preferred embodiment, the duration of the quiescent period is approximately fifteen minutes. As noted above, such preferred embodiments are optional. For example, the use of a quiescent period yielding a minimum reading, a maximum reading, or a specific predetermined reading is possible. In addition, any quiescent period duration may be used. Different ways to determine the quiescent period are possible.

In the preferred embodiment the method analyzes the incoming data stream, referred to in FIG. 2 as X(j), and starts the quiescent period identification as soon as the next X(j) has a lower value than the previously measured quiescent period concentration value. Optionally, at the beginning of each system cycle, there is no previously established quiescent period concentration value. With such an option, the first quiescent period identification starts at the beginning of every system cycle. The acquisition continues for fifteen minutes, or for whatever time period is set as a preferred quiescent period, so long as the concentration readings correspond to the desired quiescent period reading, such as readings that remain within a range of +/−20 ppm from the initial value. At the end of the predetermined time period, the averaged concentration value is calculated and established as a quiescent concentration value. In cases when the CO2 concentration does not correspond to the desired quiescent period reading (for example, where the readings do not stay within the desired +/−20 ppm range), the quiescent period identification is restarted and the method starts looking for the new minimum data in the incoming data stream. It is possible that there will be no quiescent period found during a particular cycle, in which case quiescent period identification simply continues in the next time period or cycle.

As noted above, the quiescent period preferably corresponds to the subset of the first time period during which activity in the measured environment is at a minimum, and thus the measured component concentrations are likely to be at a minimum. However, periods corresponding to maximum or predetermined concentrations may be used. The system then identifies a first component concentration, preferably corresponding to the average component concentration during the quiescent period, and adds the first component concentration to an initial set (box 36). The system then obtains gas concentration data for additional time periods. This gas concentration data may come from memory, the data thus corresponding to one or more previous time periods, or the first component concentration may be stored in memory and the gas concentration data for one or more additional time periods may be gathered in the future. Optionally and preferably, however, all of the gas concentration data is streamed to the processor in a real time from the sensor rather than retrieved from a memory. Preferably, the additional time periods are or include additional quiescent periods corresponding to additional cycles. With every cycle, a new quiescent period is detected (box 40) and a new data point is added to the processor memory (box 42). Thus the processor accumulates in its memory a number of concentration data points related to stable sensor readings. The memory content is renewed periodically as soon as the new quiescent period is detected.

When the additional component concentrations are identified, they are added to the initial set, as indicated by box 42. For a preferred embodiment the set includes fourteen points of data, and each point corresponds to one day (twenty-four hours) of the sensor operation. Every twenty-four hours (or such other appropriate period as may be determined) the same cycle is performed so that the data set contains the data for the latest fourteen days of the sensor operation. However, any number of data points, corresponding to any cycle, may be used.

The next step in the present inventive method is data validation. The data collected by the sensor and included in the data set may contain invalid or erroneous data points. For example, during power brownout periods the sensor could accumulate erroneous readings. As another example, when some service or repair activity is performed on the equipment using the gas sensor, the gas concentration may not reach expected levels. In a preferred embodiment, the algorithm establishes and applies bounds, or a range (represented by box 44 in FIG. 3), such that readings falling within the bounds or range are used in the subsequent computation of the sensor adjustment, and readings outside of the bounds or range are not used. In a preferred embodiment, the range is established by calculating the average of the concentration readings over a predetermined number of cycles, such as a set of fourteen daily data points corresponding to quiescent periods for those days, and allowing for a preset range surrounding the average. As illustration of this example:

C_average=<average over the set of 14 daily data points>

The acceptance boundaries are then calculated as:

High Bound=C_average+Predertermined_Value_1

Low Bound=C_average−Predertermined_Value_2

The data included in the data set are considered invalid if they are inside the boundaries. The invalid data are not used for further calculations. (Boxes 48, 50, and 52 in FIG. 3.) Alternatively, invalid data may be modified to correspond to a valid concentration (box 50), such as for example the midpoint or an outer boundary of the valid concentration range. This procedure preferably repeats after, or at a specified point within, every system cycle. Thus, the valid data set is revised every system cycle. In a preferred embodiment, the predetermined value 1 is set to 150 ppm, while predetermined value 2 is set to 300 ppm. However, any predetermined values may be used.

The above-described approach to data validation represents one of many possible ways of validating data, and thus boxes 44 and 48 in FIG. 4 illustrate an option used with the above-described preferred embodiment. A number of different ways may be used to validate the data included in the data set. For example, if 380 parts per million is assumed to be a normal minimum background level of $CO_2$ in an indoor ambient environment, readings falling outside of a range of, for example, 380+/−200 parts per million may be considered to be invalid. The validation method is optionally and preferably application-specific and may include different criteria for other gas sensor applications, as well as for HVAC control or other, applications when using different types of gas sensors.

Again referring to FIG. 4, the system then identifies a preset background concentration (box 54) and determines an estimated background concentration (box 56). Preferably, the preset background concentration is determined by taking an average of one or more of the valid concentrations within a concentration set. In a preferred embodiment, the estimated background concentration is calculated simply as the average of all valid data points from the data set. Alternatively, for example, the method may take the first component concentration and additional component concentrations for the next two subsequent time periods, take the average of such three concentrations, and set the estimated background concentration to the calculated average. This calculation is repeated every time cycle (such as every 24 hours). However, other methods of determining an estimated background concentration may be used, such as through linear or nonlinear filtering of data in the data set.

Once the estimated background concentration, as measured by the sensor, is known, it is compared to the preset background level to yield a correction value (box 58). The preset background level may be a predetermined value, or it may be a background level measured on a particular day. The preset background may or may not related to actual ambient air background. In addition, the preset background level may be stored in memory as a reference. On one embodiment, the comparison involves taking the difference between the preset background level and the estimated background concentration to reveal the average baseline drift of the sensor over the time period covered by the concentrations that are factored into the preset background level. The system then determines a correction value that is equal to the difference between the preset background and the estimated background, as indicated by box 58. The correction value may then be applied to every $X(j)$ to yield a corrected reading–$Xc(j)$, where $Xc(j)=X(j)+Correction$. (Box 60.) This corrected reading may trigger an event (box 62), such as turning on a blower after it is forwarded to an HVAC control in analog or digital form.

Thus, for example, if it is determined that the baseline of the sensor has, through drift, added an average of 100 parts per million to each measurement, then measurements taken after that determination will be reduced by 100 parts per million to yield correct data. The event may also be in the case when the correction value exceeds a certain level, an indication to the system operator that the sensor drifted too much and it needs service or replacement.

Alternatively the estimated background concentration data can be used for span drift correction. In such a case, rather than taking the difference between the preset background level and the estimated background level, to calculate the correction value (box 58) the system takes the ratio of the preset background level to the estimated background concentration to be the correction value. Illustrating this example: Correction=(preset background level)/(est. background concentration). This ratio may used as a correction coefficient, which used to adjust every X((j) by the formula Xc(j)=X((j)*Correction. (Box 60.)

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method of compensating for drift of a gas sensor, comprising:
    (a) providing a processor with gas concentration data relating to a first period of time;
    (b) identifying a quiescent period, the quiescent period being a subset of the first period of time, the gas concentration data including quiescent period data relating to the quiescent period;
    (c) determining a first component concentration wherein the quiescent period has a duration, and if the duration is less than a minimum duration, the first component concentration is omitted from the valid concentration set;
    (d) providing the processor with a least one additional component concentration, each additional component concentration corresponding to a separate and distinct time period, wherein the first component concentration and the additional component concentrations provide an initial concentration set;
    (e) selecting, by the processor, at least one valid concentration from the initial concentration set to yield a valid concentration set;
    (f) providing the processor with a preset background value;
    (g) calculating, by the processor, an estimated background value; and
    (h) calculating, by the processor, a correction value comprising a function of the preset background value and the estimated background value.

2. The method of claim 1 wherein the function comprises the difference between the preset background value and the estimated background value.

3. The method of claim 1 wherein the function comprises the ratio of the preset background value to the estimated background value.

4. The method of claim 1 comprising the additional step of detecting a measured component concentration and adjusting the measured component concentration, the adjustment corresponding to the correction value, to yield an adjusted component concentration.

5. The method of claim 1 wherein the quiescent period has a duration, the duration is equal to or greater than a minimum duration, and the first component concentration related to the quiescent period data.

6. The method of claim 1, wherein the first component concentration does not correspond to predetermined value or range or criteria, and the first component concentration is omitted from the valid concentration set.

7. The method of claim 6, wherein the predetermined value relates to one or more of the additional component concentrations.

8. The method of claim 1 wherein the estimated background concentration corresponds to the valid concentration in the valid concentration set.

9. The method of claim 1 comprising the additional step of triggering an event or selecting a restriction if the correction value exceeds a trigger value.

10. A system for compensating for gas sensor drift comprising:
    a processor and a memory for string data to be processed by the processor, the processor programmed to perform the following functions:
        (a) accepting gas concentration data relating to a first time period;
        (b) identifying a quiescent period, the quiescent period being a subset of the first time period, the gas concentration data including quiescent period data relating to the quiescent period;
        (c) determining a first component level wherein the quiescent period has a duration, and if the duration is less than a minimum duration, the first component level is omitted from the valid concentration set;
        (d) accepting from data stored in the memory at least one additional component level, each additional component level relating to an additional time period;
        (e) providing an initial component set comprising at least one of the first component level and one or more of the additional component levels;
        (f) selecting at least one valid component level from the initial component set to yield a valid component set;
        (g) accepting from the data stored in the memory a preset background level;
        (h) calculating an estimated background level; and
        (i) calculating a correction value.

11. The system of claim 10 wherein the correction value comprises the difference between the preset background level and the estimated background level.

12. The system of claim 10 wherein the correction value comprises the ratio of the preset background level to the estimated background level.

13. The system of claim 10 wherein the first component level relates to the quiescent period data.

14. The system of claim 10 wherein the estimated background level corresponds to the valid component levels in the valid component set.

15. The system of claim 10 wherein the processor is also programmed to perform the step of detecting a measured component concentration and adjusting the measured component concentration, the adjustment corresponding to the correction value, to yield an adjusted component concentration.

16. The system of claim 10 wherein the processor is also programmed to perform the step of triggering an event if the correction value exceeds a trigger value.

17. A method of compensating for the drift of gas sensing equipment comprising:
    (a) gathering gas concentration data relating to a plurality of time periods;
    (b) identifying a plurality of quiescent periods, each quiescent period being a subset of the one of the time periods, the gas concentration data relating to each time period including quiescent period data relating to the corresponding quiescent period, the quiescent period data including data corresponding to a background concentration;

(c) collecting the background concentrations for each quiescent period in an initial set wherein the quiescent period has a duration, and if the duration is less than a minimum duration, the background concentrations are omitted from the valid concentration set;

(d) validating the background concentrations in the initial concentration set to yield valid concentrations in a valid concentration set;

(e) identifying a first component level;

(f) calculating a second component level corresponding to the valid concentrations in the valid concentration set;

(g) calculating a correction value corresponding to a function of the first component level and the second component level; and (h) detecting a measured component concentration and adjusting the measured component concentration corresponding to the correction value to yield an adjusted component concentration.

18. The method of claim 17 wherein the function in the calculating step is a difference or a ratio.

19. A system for compensating for gas sensor drift comprising:

a gas sensor for determining gas concentration data; and means for processing said gas concentration data, said processing means including identification means for identifying quiescent periods and gas concentration data related to said quiescent periods, wherein the quiescent period has a duration, and if the duration is less than a minimum duration, the gas concentration data is omitted from the valid concentration set, component level determination means for determining valid component levels from said gas concentration data, and correction value calculating means for calculating a correction value from stored preset background level gas concentration data and estimated background level concentration data.

* * * * *